United States Patent

Kakoki et al.

[11] Patent Number: 5,415,875
[45] Date of Patent: May 16, 1995

[54] ANTI-PEROXIDE EXTERNAL PREPARATION FOR SKIN

[75] Inventors: Hiroyuki Kakoki; Yoshiyuki Kono; Shinichiro Funatsu; Masaaki Komatsu, all of Yokohama, Japan

[73] Assignee: Shiseido Co., Ltd., Tokyo, Japan

[21] Appl. No.: 139,850

[22] Filed: Oct. 22, 1993

[51] Int. Cl.$^6$ .............. A61K 35/00; A61K 31/355; A61K 7/48

[52] U.S. Cl. ...................... 424/581; 424/45; 424/401; 514/458; 514/828; 514/844; 514/846; 514/887; 514/937; 514/938; 514/969

[58] Field of Search ............... 424/401, 581, 45, 828, 424/581; 514/844, 846, 887, 937, 938, 969, 458

[56] References Cited

PUBLICATIONS

JP 3258709 (Abstract). Nov. 1991.
JP 3255018 (Abstract) Mar. 1990
JP 63254180 (Abstract) Oct. 1988
Remington's Pharmaceutical Sciences, p. 1008 (1985).

Primary Examiner—Jyothsna Venkat
Attorney, Agent, or Firm—Townsend & Banta

[57] ABSTRACT

An anti-peroxide external preparation for skin comprising: decomposition product of shell membrane: and tocopherol and/or derivatives thereof. It is possible to suppress formation of peroxide and remove it.

2 Claims, 2 Drawing Sheets

ANTI-PEROXIDE EXTERNAL PREPARATION FOR SKIN

FIELD OF THE INVENTION

This invention relates to an external preparation for skin, and more particularly to an improvement of the external preparation for skin having suppressing effect on lipid peroxide formation and removing effect on the lipid peroxide.

BACKGROUND ART

Lipid peroxide, which is produced by oxidization of the lipid, has various influences to human body such as a cytotoxic effect. Therefore, it is necessary to suppress formation of lipid peroxide for maintaining the human body normally. In the human body, an anti-oxidation function is provided originally.

However, the anti-oxidation function of the human body declines with aging. Especially, at the skin which is always exposed to stress from outside, it is admitted that amount of the lipid peroxide in the skin increases according to the aging. It is thought that the increasing of the lipid peroxide is one of causes of the skin degradation.

Maintaining youthful skin forever is an eternal object, and suppressing the formation of the lipid peroxide in the skin is important.

As the substances which suppress the formation of lipid peroxide, BHA, BHT and so on are known. However, these substances which have higher effect have problems in the safety when the substances are applied to the skin long-term.

On the other hand, vitamins such as ascorbic acid and tocopherol which can be utilized for cosmetics have not a problem in the safety. However, because coloring is admitted in the ascorbic acid when the preparation is preserved for long-time, it is possible to add the ascorbic acid into the preparation only in a small amount. Also, the tocopherol can remove radical caused in the process of lipid peroxide's formation. Therefore, the effect which suppress the formation of the lipid peroxide in the skin is admitted concerning the tocopherol. However, the function to remove existing lipid peroxide is not provided with the tocopherol. As described above, the tocopherol is also not enough as the anti-peroxide substances.

DISCLOSURE OF THE INVENTION

Accordingly, it is an object of the present invention to eliminate the above-described problems in the prior art and to provide an external preparation for skin which can suppress formation of the lipid peroxide and remove the peroxide more efficiently.

As a result of studies undertaken by the present inventors so as to achieve this aim, it has been found that an improvement of suppressing effect on the lipid peroxide and removing effect on the same can be observed in coexistence of a decomposition product of shell membrane and tocopherol. The present invention has been achieved on the basis of the finding.

The structure of the present invention will be explained in detail hereinafter.

An amount of the decomposition product of shell membrane in an external preparation for skin according to the present invention is available in extremely small amount, and preferably 0.00005 to 0.5 wt % and more preferably 0.0001 to 0.05 wt %. It is suggested that the decomposition product of shell membrane reacts as a catalyst because the suppressing effect on the peroxide formation and removing effect on the existed peroxide can be observed in such small amount and relatively for long period.

If the amount of the decomposition product of shell membrane is less than 0.00005 wt %, the function may not be obtained. Addition of more than 0.5 wt % of the decomposition product of shell membrane hardly increases the effect.

The amount of tocopherol and/or the derivatives thereof in the external preparation for skin according to the present invention is preferably 0.005 to 5.0 wt % and more preferably 0.01 to 3.0 wt %.

If the amount of tocopherol and/or the derivatives thereof is less than 0.005 wt %, it is sometimes impossible to obtain a sufficient effect. Addition of more than 5.0 wt % of the tocopherol and/or the derivatives thereof hardly increases the effect.

The decomposition product of shell membrane is prepared by, as described in the JAPANESE PATENT LAID OPEN No.3-258709, that a membrane which is adhered inside of eggshell of aves egg such as an egg, a quail egg (the shell membrane) is dissolved in a solvent such as water and alcohol. The decomposition product is prepared, for example, by solubilizing the shell membrane with acid, alkali, an organic solvent, an oxidase and a reductase.

Namely, the decomposition product is obtained by decomposition process in alkaline hydrating organic solvent. As examples of the alkaline hydrating organic solvent, mixture of 70 to 40% of an alkali solution which is prepared by adding alkaline such as sodium hydroxide and potassium hydroxide so as to the alkaline concentration thereof be 0.2–3.0N, and 30–60% of water soluble organic solvents such as methanol, ethanol and acetone. The decomposition condition is preferably 1 to 8 hours at 30°–60° C. The solution of the soluble shell membrane is obtained by neutralizing and filtering the solubilized liquid.

On the other hand, as examples of the tocopherol and the derivatives thereof, $\alpha$-tocopherol, tocopherol acetate, DL-$\alpha$-tocopherol nicotinate, DL-$\alpha$-tocopherol succinate and so on are given.

In addition to the above-described essential ingredients, it is possible to add, if necessary, other ingredients which are used for ordinary cosmetics, drugs or quasi-drugs for application to skin. Those ingredients are, for example, vitamin A's such as vitamin A oil, retinol and retinol acetate; vitamin $B_2$'s such as riboflavin, riboflavin butyrate and flavin adenine dinucleotide; vitamin $B_6$'s such as pyridoxine hydrochloride and pyridoxine dioctanoate; vitamin C's such as L-ascorbic acid, dipalmitate L-ascorbate, Na L-ascorbate-2-sulfate; pantothenic acids such as calcium pantothenate, D-pantothenyl alcohol, pantothenyl ethyl ether and acetylpantothenyl ethyl ether; vitamin D's such as ergocalciferol and cholecalciferol; nicotinic acids such as nicotinic acid, nicotinic acid amide, benzyl nicotinate; vitamin E's such as $\alpha$-tocopherol, tocopherol acetate, DE-$\alpha$-tocopherol nicotinate and DL-$\alpha$-tocopherol succinate; other vitamins such as vitamin P and biotin; amino acids and derivatives thereof such as glycine, alanine, valine, leucine, isoleucine, serine, threonine, aspartic acid and salts thereof, glutamic acid and salts thereof, lysine, arginine, cysteine, methionine, phenylalanine, tyrosine, histidine, tryptophane, proline, N-acyl acidic amino acid salts such as diethyl-N-palmitoyl L asparaginate and sodium N-coconut oil fatty acid-L-glutamate; acyl neutral amino acid salts such as coconut oil fatty acid-sarcosine triethanol amine and laurolylmethyl-$\beta$-alanine sodium; pyrrolidonecarboxylic acid and salts thereof, POE (40) hardened castor oil monopyrrogultamic monoisostearic diester and coconut oil fatty acid-L-ethyl arginate-DL-pyrrolidonecarboxylate; oil contents such as avocado oil, palm oil, peanut oil, beef tallow, rice bran oil, jojoba oil, evening primrose oil, carnauba wax, lanolin, liquid paraffin, squalane, isostearyl palmitate, isostearyl alcohol and glycerin tri-2-ethylhexanate; humectants such as glycerin, sorbitol, polyethylene glycol, 1, 3-butylene glycol, collagen, hyaluronic acid, chondroitin sulfuric acid and sodium dextran sulfate; antioxidants such as sodium erisorbate and parahydroxyanisole; surfactants such as sodium stearyl sulfate, cetyl sulfate diethanol amine, cetyl trimethyl ammonium saccharin, polyethylene glycol isostearate, glyceryl arachate, diglycerin diisostearate and phospholipid; antiseptic agents such as ethyl para-hydroxybenzoate and butyl para-hydroxybenzoate; antiphlogistic agents such as glycyrrhizic acid, glycyrrhetic acid, salicylic acid derivative, hinokitiol, zinc oxide and allantoin; skin beautifiers such as extract of placenta, glutathione and extract of creeping saxifrage; various extracts such as extracts of phellodendron bark, goldthread, peony, Japanese green gentian, birch, sage, loquat, ginseng, aloe, mallow, iris, grape, coix seed, dishcloth gourd, lily, saffron, Cnidium officinare Makino, giner, Saint-John's wort, rosemary and garlic, vitalizers such as royal jelly, sensitizing dye, cholesterol derivatives and extract of calf's blood; blood circulation facilitators such as $\gamma$-oryzanol; anti-srborrhoeic agents such as sulfur and thianthol; thickening agents such as carboxyvinyl polymers, carboxymethyl cellulose and carboxylhydroxypropyl cellulose; perfumes; water; alcohols; coloring agents such as titanium yellow, carthamin and safflower red: and resin powder such as polyethylene and nylon powders.

In the present invention, if an ultraviolet absorbent is used in addition to the essential ingredients, the suppressing effect on peroxide is improved.

As the ultraviolet absorbent, ultraviolet absorbents which are permitted as ingredients of ordinary cosmetics are used as occasion demands. Examples thereof are:

cinnamic acid ultraviolet absorbents such as 2-ethoxyethyl paramethoxy cinnamate, isopropyl paramethoxy cinnamate, diisopropyl cinnamate, ethylhexyl paramethoxy cinnamate, glyceryl diparamethoxy cinnamate mono-2-ethyl hexanoate and octyl methoxy cinnamate;

benzoylmethane ultraviolet absorbents such as butylmethoxybenzoylmethane and 4-tert-butyl-4'-methoxydibenzoylmethane;

benzophenone ultraviolet absorbents such as glyceryl-mono-2-ethylhexanoyl-di-paramethoxybenzophenone, 2-2'-dihydroxy-4-methoxybenzophenone, 2-2'-dihydroxy-4,4'-dimethoxybenzophenone, 2-hydroxy-4-methoxybenzophenone and sodium 2-hydroxy-4-methoxybenzophenone-5-sulfonate;

benzoic acid ultraviolet absorbents such as methyl orthoaminobenzoate, 2-ethylhexyl-paradimethyl aminobenzoate and octyl paradimethyl aminobenzoate;

benzoate ultraviolet absorbents such as grycelyl paraaminobenzoate, amyl-para-dimethyl aminobenzoate and ethyl-4-bishydroxy propyl aminobenzoate; and other ultraviolet absorbents such as 2-ethylhexyl-2-cyano-3, 3'-diphenyl acrylate, digalloyl trioleate, 2-ethylhexyl salicylate, homomethyl salicylate, guaiazulene and urocanic acid.

The amount of ultraviolet absorbent added is different depending upon the type of ultraviolet absorbent, but it is generally 0.01 to 15.0 wt % of the total amount of external preparation.

If the amount of ultraviolet absorbent is less than 0.01 wt %, the effect is sometimes insufficient. Addition of more than 15.0 wt % of ultraviolet absorbent hardly increases the cutaneous aging resisting effect.

The external preparation according to the present invention may take any given form. For example, it may be a soluble agent such as lotion, an emulsified agent such as milky lotion and cream, an ointment, a dispersant or an aerosol.

EXAMPLES

Examples of the present invention will be explained hereinafter. However, this invention is never limited to the examples.

Preparation of Decomposition Product of Shell Membrane

First, the preparation example of the soluble shell membrane is explained.

After removing albumen and yolk, an eggshell with the shell membrane was putted into water. The eggshell was removed with the hand and obtained a shell membrane. The membrane was dipped in 1% hydrochloric acid aqueous solution for one hour and removed small eggshells which were adhered on the shell membrane. The shell membrane was washed with water, sun-dried and the dried shell membrane was obtained.

100 g of the dried shell membranes was added into 1200 ml of 2N sodium hydroxide aqueous solutions and 800 ml of dehydrated ethanols and stirred for 5 hours at 40° C. In this reaction, the shell membrane was liquidized. After the obtained liquid was filtrated with a cloth filter, neutralized and desalted, 1% water solution of decomposition product was obtained.

Anti-Peroxide Effect Examination

By using the above obtained 1% aqueous solution of soluble shell membranes and tocopherol, examination about the suppressing effect on the lipid peroxide formation and the lipid peroxide removing effect were conducted.

Suppressing Effect on Lipid Peroxide Formation

Peroxide reaction of purified squalene under existence of samples and UV irradiation was investigated.

The sample solution (80% of ethanol bases) were applied to cover glasses and and removed the solvent (0.2mg/cm$^2$ on the cover glasses approximately correspond to the amount of which an external preparation for skin is applied to skin). After drying the sample, purified squalene was dropped on it.

Ultraviolet ray was irradiated for 1 hour and the squalene was collected with solvent. Amount of the squalene hydroperoxide as the lipid peroxide was measured by CL-HPLC method.

Figure 1:
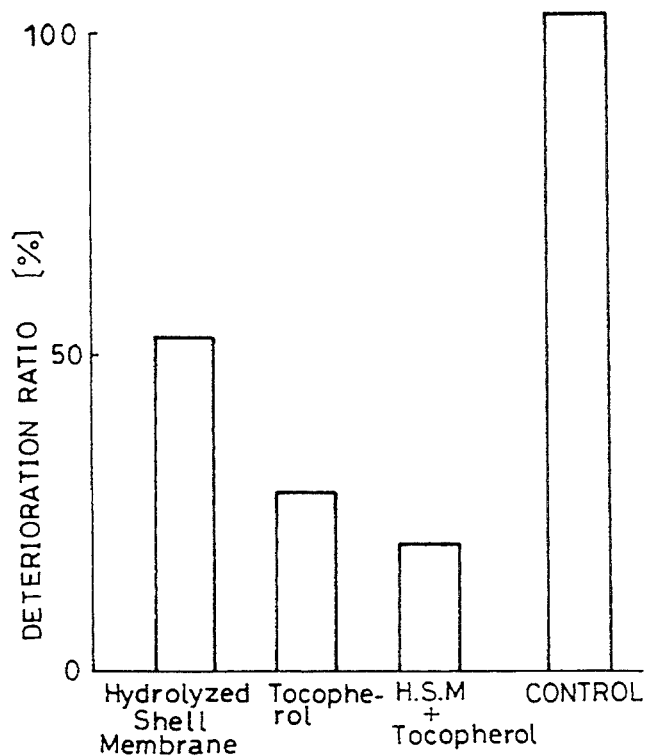
FIG. 1 is an explanatory view of the reinforcement of suppression effect on tocopherol formation of the lipid peroxide by adding the hydrolyzed shell membrane.

A result was shown in the FIG. 1.

As is clear from the figure, the lipid peroxide formation was suppressed to about 30% comparing the system including α-tocopherol so as to be 200 ppm with the control including no substances.

Also, in the system including the hydrolyzed shell membrane so as to be 200 ppm, the suppress effect on lipid peroxide formation was about 50%.

However, when 100 ppm of both substances were contained, the lipid peroxide formation was suppressed to about 20%.

From the result, it is expected that a synergistic effect on suppressing the lipid peroxide formation was existed in coexistence of the hydrolyzed shell membrane and the α-tocopherol.

Further, the present inventors carried out the examination of change of the lipid peroxide amount with time under the similar experiment system.

Figure 2:
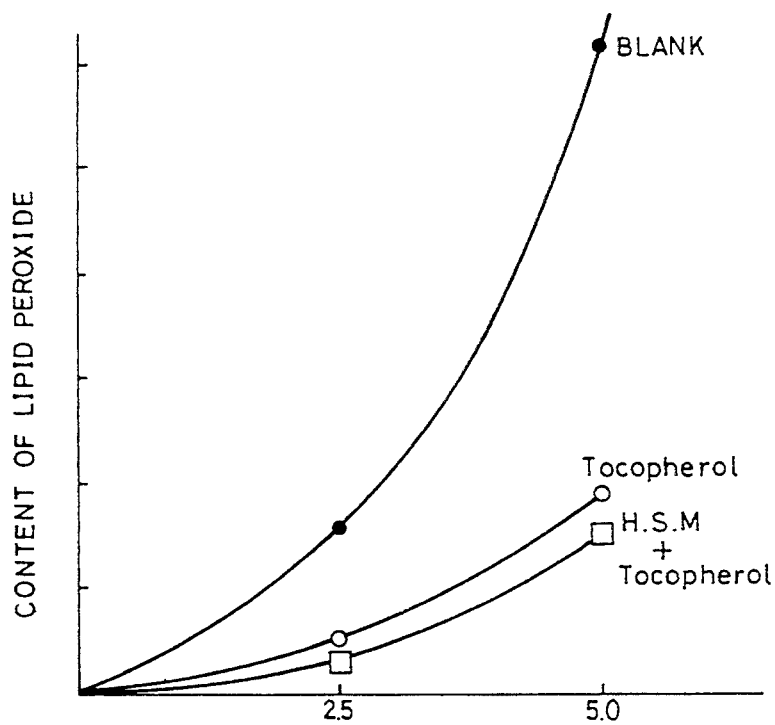
FIG. 2 is an explanatory view of change of the lipid peroxide formation with time when tocopherol only, and both of tocopherol and the hydrolyzed shell membrane exist.

As a result shown in FIG. 2, by adding the α-tocopherol so as to be 100 ppm, the formation curve of lipid peroxide shifts down, and by the coexistence system with the hydrolyzed shell membrane, the curve shifts further down.

Therefore, it is understood that there is an enhancement of suppressing effect on lipid peroxide formation by adding the hydrolyzed shell membrane to the tocopherol.

Lipid Peroxide Removing Effect

Amount of the squalene hydroperoxide under the existence of sample in room temperature was investigated.

Namely, using a photosensitized oxidation reaction, squalene hydroperoxide was synthesized from purified squalene.

On the other hand, each sample solution (80% of ethanol bases) was applied on the cover glasses as described above and dried. And then, squalene solution of the squalene hydroperoxide were dropped on the cover glasses and analyzed squalene hydroperoxide amount in it after the 2.5 hours by the CL-HPLC method.

Figure 3:
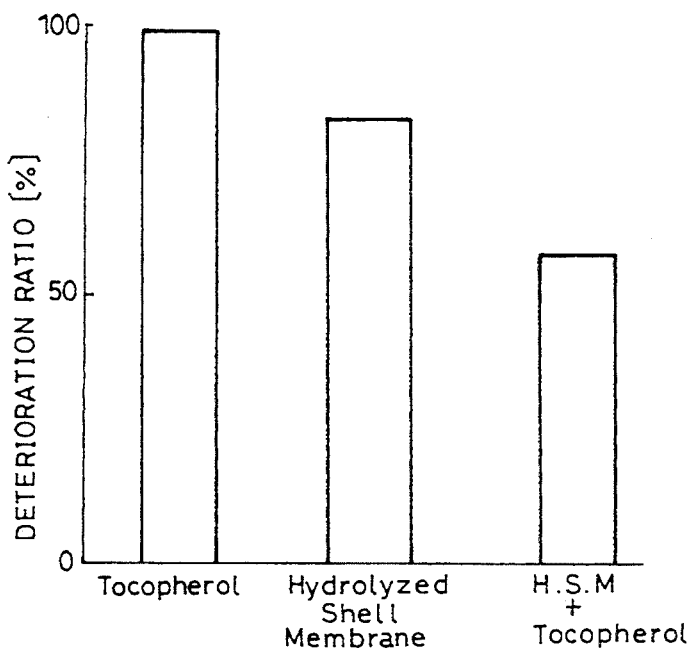
FIG. 3 is an explanatory view of lipid peroxide removing effect by tocopherol, the hydrolyzed shell membrane, and coexistence of both; and, FIG. 4 is an explanatory view of change of the lipid peroxide amount with age when tocopherol only, the hydrolyzed shell membrane only, coexistence of both.

A result is shown in the FIG. 3.

As is clear from the figure, the removing effect on the lipid peroxide hardly observed in the tocopherol itself. Also, about 20% of removing effects were observed in the hydrolyzed shell membrane. However, when both substances coexisted, an excellent removing effect on the lipid peroxide (about 40%), which wasn't seen in the each independent substance respectively, was admitted.

Using a similar experiment system, the change of the lipid peroxide amount with time was observed.

Figure 4:
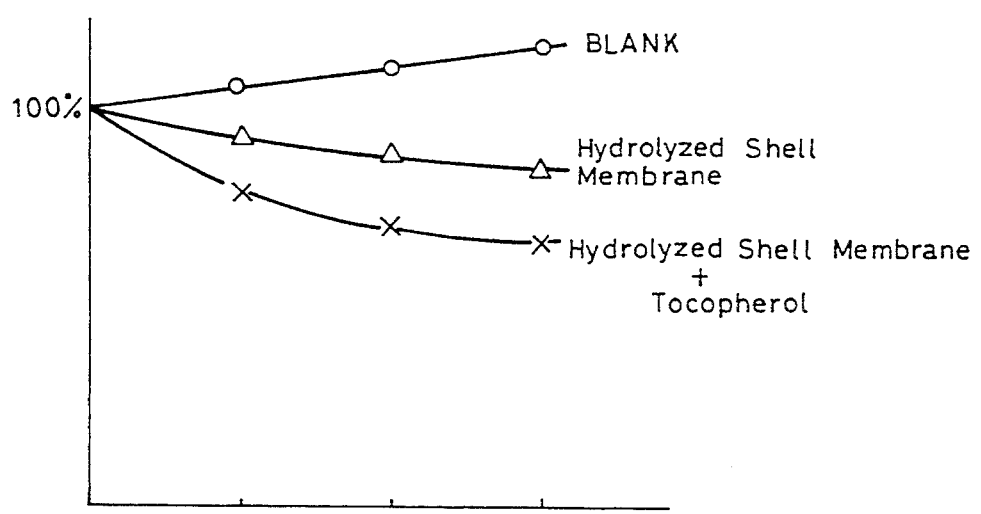

A result is shown in the FIG. 4.

As is clear from the figure, in case of the existence of the hydrolyzed shell membrane only, the lipid peroxide decreases according to the time but became a stationary state approximately at about However, when tocopherol is coexisted, the decrease ratio is improved to about 60%.

From the experiment result, even if tocopherol is independently used, the suppressing effect on lipid peroxide formation is expected by the function as the radical scavenger which tocopherol originally has. However, it is improved synergisticly by the coexistence of the hydrolyzed shell membrane. Moreover, while the necessary amount of the hydrolyzed shell membrane is a small amount, the hydrolyzed shell membrane made the lipid peroxide formation to be delayed. Therefore, the hydrolyzed shell membrane itself isn't consumed for suppressing the lipid peroxide formation and it is understood that the hydrolyzed shell membrane reinforces the effect of tocopherol like a catalyst.

Also, the removing effect on lipid peroxide which is already existed is not observed in the tocopherol and the lipid peroxide removing effect of the hydrolyzed shell membrane is very week. Namely, it is not observed in the tocopherol that the effect on decomposing and removing the lipid peroxide. On the other hand, although the ability to decompose the lipid peroxide is existed in the hydrolyzed shell membrane, the ability is catalytic. Therefore, it isn't possible to decompose the peroxide any more if the amount of the peroxide and that of the decomposed product reach to chemical equilibrium condition. In the case of the hydrolyzed shell membrane and tocopherol coexisting in the system, the hydrolyzed shell membrane decomposes hydroperoxide residue in lipid peroxide in homolytic reaction. The radical which is produced by the decomposition reaction is caught by the tocopherol. As a result, the coexistence of the hydrolyzed shell membrane and tocopherol shows the excellent removing ability for the lipid peroxide which hardly exists in the tocopherol or in the hydrolyzed shell membrane respectively.

Contents

The present inventors examined preferred content of the hydrolyzed shell membrane and the tocopherol.

Content of Hydrolyzed Shell Membrane

The necessary content of the hydrolyzed shell membrane is examined according to the removing effect on the lipid peroxide.

A result is shown in the table 1.

TABLE 1

| α-tocopherol | | | | 1% | | | | |
|---|---|---|---|---|---|---|---|---|
| Hydrolyzed shell membrane | 0 | 0.00001 | 0.00005 | 0.0001 | 0.0005 | 0.5 | 1.0 | 3.0 |
| Survival rate of lipid peroxide | 100 | 95 | 70 | 62 | 62 | 60 | 60 | 60 |

As a result, the content of the hydrolyzed shell membrane is preferably equal to or more than 0.00005 wt %. However, addition of more than 0.5 wt % hardly increases the effect.

Content of Tocopherol

The necessary content of the tocopherol is examined according to the removing effect on the lipid peroxide.

A result is shown in the table 2.

TABLE 2

| α-tocopherol | 0.001 | 0.005 | 0.01 | 0.05 | 0.1 | 0.5 | 1.0 | 5.0 |

TABLE 2-continued

| | | | | | | | | |
|---|---|---|---|---|---|---|---|---|
| Hydrolyzed Shell membrane | | | | 0.0001 | | | | |
| Survival rate lipid peroxide | 80 | 72 | 60 | 60 | 63 | 60 | 59 | 60 |

As a result, the content of the tocopherol is preferably equal to or more than 0.005 wt %. However, addition of more than 5.0 wt % hardly increases the effect and sometimes get worse usability of the preparation.

The example of the external preparation for skin according to the present invention will be explained hereinafter.

EXAMPLE 1

Water in Oil Type Emulsified Cosmetic

| <Aqueous part> | |
|---|---|
| Glycerol | 15.0 weight % |
| 1,3-butylene glycol | 5.0 |
| Distearyldimethylammomiumhectrite chloride | 2.1 |
| Dimethylpolysiloxane polyethylene glycol | 2.1 |
| 1% Aqueous solution of hydrolyzed shell membrane | 0.01 |
| Ion exchanged water | balance |
| <Oil part> | |
| Liquid paraffin | 5.0 |
| Vaseline | 1.0 |
| Cetyl 2-ethyl hexanoate | 5.0 |
| Methyl polysiloxane | 5.0 |
| Cyclo polydimethylsiloxane | 10.0 |
| Ethylparaben | 0.2 |
| Butylparaben | 0.1 |
| Tocopherol acetate | 0.07 |

Manufacturing method

The aqueous part and the oil part are dissolved at 70° C., respectively. The aqueous part was added into the oil part. The system was stirred, emulsified and cooled to the room temperature.

EXAMPLE 2

Oil in Water Type Emulsified Cosmetic

| <Aqueous part> | |
|---|---|
| Glycerol | 6.0 weight % |
| 1,3-butylene glycol | 9.0 |
| Glycerol POE(60) monoisostearate | 1.3 |
| Lipophilic type glyceryl monostearate | 1.6 |
| Self emulsifying propylene glycol monostearate | 1.0 |
| 1% Aqueous solution of hydrolyzed shell membrane | 0.01 |
| Ion exchanged water | Balance |
| <Oil part> | |
| Cetostearyl alcohol | 3.6 |
| Liquid paraffin | 3.0 |
| Vaseline | 2.5 |
| Cetyl 2-ethyl hexanoate | 3.0 |
| Methyl polysiloxane | 1.5 |
| Ethylparaben | 0.1 |
| Butylparaben | 0.1 |
| Tocopherol acetate | 0.07 |

Manufacturing method

The aqueous part and the oil part are dissolved at 70° C., respectively. The oil part was added into the aqueous part. The system was stirred, emulsified and cooled to the room temperature.

EXAMPLE 3

Lotion

| <Aqueous part> | |
|---|---|
| 1% Aqueous solution of hydrolyzed shell membrane | 0.05 |
| Sodium 2-hydroxy 4-ethoxybenzophenone 5-sulfonate | 0.1 |
| Glycerin | 4.0 |
| 1,3-butylene glycol | 4.0 |
| Citric acid | 0.05 |
| Sodium citrate | 0.1 |
| Purified water | balance |
| <Ethanol part> | |
| Tocopherol acetate | 0.01 |
| Ethanol | 8.0 |
| Polyoxyethylene (60) hardened castor oil | 0.5 |
| Methyl para-hydroxybenzoate | 0.2 |
| Perfume | 0.05 |

Process

1% Aqueous solution of hydrolyzed shell membrane, sodium 2-hydroxy-4-methoxybenzophenone-5-sulfonate, citric acid, sodium citrate, glycerin and 1, 3-butylene glycol were dissolved in purified water. Separately from this, polyoxyethylene (60) hardened castor oil, tocopherol acetate, perfume and methyl para-hydroxybenzoate were dissolved in ethanol. The latter solution was added to the purified water solution for solubilization, and the resultant solution was filtered to obtain lotion.

EXAMPLE 4

Cream

| <Oil part> | |
|---|---|
| Tocopherol acetate | 1.0 |
| Cetostearyl alcohol | 3.5 |
| Squalane | 40.0 |
| Bee wax | 3.0 |
| Reduced lanolin | 5.0 |
| Ethyl para-hydroxybenzoate | 0.3 |
| Polyoxyethylene (20) sorbitan mono palmitate | 2.0 |
| Monoglyceride stearate | 2.0 |
| Sodium N-stearoyl glutamate | 0.5 |
| 2-hydroxy-4-methoxy-benzophenone | 0.5 |
| Octyl methoxycinnamate | 1.0 |
| Retinol acetate | 2.0 |
| Evening primrose oil | 0.05 |
| Perfume | 0.03 |
| <Aqueous part> | |
| 1% Aqueous solution of hydrolyzed shell membrane | 0.1 |
| 1,3-butylene glycol | 5.0 |
| Polyethylene glycol 1500 | 5.0 |
| Purified water | balance |

Process

Tocopherol acetate, cetostearyl alcohol, squalane, bee wax, reduced lanolin, ethyl para-hydroxybenzoate, polyoxyethylene (20) sorbitan monopalmitate, monoglyceride stearate, sodium N-stearoyl glutamate, 2-hydroxy-4-methoxy-benzophenone, octyl methoxycinnamate, retinol acetate and evening primrose oil were dissolved under heating. Separately from this, 1% Aqueous solution of hydrolyzed shell membrane-Na, 1,3-butylene glycol and polyethylene glycol 1500 were heated to 75° C. These liquids were added to purified water under stirring. After pulverizing the emulsified particles by a homomixer, the mixture was rapidly cooled under stirring to produce cream.

EXAMPLE 5

Milky lotion

| <Aqueous part> | |
|---|---|
| 1% Aqueous solution of hydrolyzed shell membrane | 0.2 |
| L-arginine | 0.3 |
| Na L-glutamate | 0.02 |
| Na hyaluronate | 0.01 |
| Propylene glycol | 5.0 |
| Glycerin | 3.0 |
| Carboxyvinyl polymer | 0.12 |
| PCA-Na | 0.05 |
| Purified water | balance |
| <Oil part> | |
| 2-ethylhexyl para-dimethylaminobenzoate | 0.1 |
| Mono-2-ethylhexyl diparamethoxycinnamate | 0.2 |
| Stearic acid | 1.5 |
| Cetyl alcohol | 0.5 |
| Bee wax | 2.0 |
| Polyoxyethylene (10) monooleate | 2.0 |
| Ethyl para-hydroxybenzoate | 0.3 |
| Tocopherol acetate | 0.05 |
| <Ethanol part> | |
| Ethanol | 3.0 |
| Perfume | 0.03 |

Process

Perfume was dissolved in ethanol (alcohol part). 1% Aqueous solution of hydrolyzed shell membrane, L-arginine, Na L-glutamate, PCA-Na, Na hyaluronate, propylene glycol, glycerin and carboxyvinyl polymer were dissolved in purified water under heating and the mixture was held at 70° C. (water part). The other ingredients were mixed and dissolved under heating, and the mixture was held at 70° C. (oil part). The oil part was added to the water part for preliminary emulsification and the mixture was uniformly emulsified by a homomixer. The alcohol part was added to the emulsion under stirring. The mixture was cooled to 30° C. under stirring to obtain milky lotion.

EXAMPLE 6

Foam mask

| | |
|---|---|
| 1% Aqueous solution of hydrolyzed shell membrane | 0.02 |
| Glycerin | 5.0 |
| 1,3-butylene glycol | 5.0 |
| Polyethylene glycol 1500 | 3.0 |
| Potassium hydroxide | 0.15 |
| Purified water | balance |
| <Oil part> | |
| 4-tert-butyl-4'-methoxy-dibenzoylmethane | 0.5 |
| Stearic acid | 1.0 |
| Behenylic acid | 1.0 |
| Self-emulsification type glycerin monostearate | 1.5 |
| Polyoxyethylene monostearate | 2.5 |
| Batyl alcohol | 1.5 |
| Perfume | 0.05 |
| Methyl para-hydroxybenzoate | 0.1 |
| Liquified petroleum gas | 6.0 |
| Dimethyl ether | 2.0 |

| -continued | |
|---|---|
| Tocopherol acetate | 0.1 |

Process

1% Aqueous solution of hydrolyzed shell membrane, glycerin, 1,3-butylene glycol, polyethylene glycol 1500, methyl para-hydroxybenzoate and potassium hydroxide were added to purified water and dissolved under heating at 70° C. The other ingredients except under heating, added to the mixture and uniformly mixed. The resultant mixture was charged in a container. Finally, liquefied petroleum gas and dimethyl ether were added to the mixture as a spraying agent, thereby producing a foam mask.

EXAMPLE 7

Ointment

| <Aqueous part> | |
|---|---|
| 1% Aqueous solution of hydrolyzed shell membrane | 0.1 |
| Purified water | balance |
| <Oil part> | |
| Octyl paradimethyl aminobenzoate | 4.0 |
| Butylmethoxybenzoylmethane | 4.0 |
| Tocopherol acetate | 0.5 |
| Retinol palmitate | 1.0 |
| Stearyl alcohol | 18.0 |
| Japan wax | 20.0 |
| Polyoxyethylene (10) monooleate | 0.25 |
| Glycerin monostearate | 0.3 |
| Vaseline | 32.0 |

Process

1% Aqueous solution of hydrolyzed shell membrane was added to purified water and the mixture was held at 70° C. (water part). The other ingredients were mixed and dissolved at 70° C. (oil part). The oil part was added to the water part and the mixture was uniformly emulsified by a homomixer. The mixture was then cooled to obtain ointment.

As described above, according to the external preparation of the present invention, since decomposition product of shell membrane and tocopherol and/or derivatives thereof are contained, it is possible to suppress the peroxide formation and further remove the peroxide.

What is claimed is:

1. A method of suppressing formation of lipid peroxide and removing peroxide comprising applying to the skin a preparation comprising:
    decomposition product of shell membrane in an amount of 0.00005 to 0.5 weight percent and tocopherol and derivatives selected from the group consisting of alpha-tocopherol, tocopherol acetate, DL-alpha tocopherol nicotinate and DL-alpha tocopherol succinate in an amount of 0.005 to 5.0 weight percent.

2. A method according to claim 1, further comprising a cosmetic base selected from the group consisting of a soluble agent, an emulsifying agent, an ointment, a dispersant and an aerosol.

* * * * *